United States Patent [19]

Tull et al.

[11] 3,998,875
[45] Dec. 21, 1976

[54] PROCESS OF PREPARING 5-FLUORO-2-METHYL-1-(PARAMETHYL-SULFINYLBENZYLIDENE)-INDENYL-3-ACETIC ACID

[75] Inventors: Roger J. Tull, Metuchen; David G. Melillg, Scotch Plains, both of N.J.

[73] Assignee: Merck & Co., Inc., Rahway, N.J.

[22] Filed: Oct. 2, 1974

[21] Appl. No.: 511,349

[52] U.S. Cl. ............... 260/515 A; 260/343.6; 260/516; 260/521 H
[51] Int. Cl.$^2$ .......................... C07C 147/14
[58] Field of Search ............... 260/515 A

[56] References Cited

UNITED STATES PATENTS 3,532,752  10/1970  Shen ............................ 260/515
3,547,923  12/1970  Standridge et al. ............ 260/268
3,654,349  4/1972  Shen et al. .................... 260/515
3,870,753  3/1975  Tull et al. ..................... 260/515

OTHER PUBLICATIONS

Rastogi, Indian J. of Chem., vol. 9 (11/71) pp. 1183–1186.

Primary Examiner—Jane S. Myers
Attorney, Agent, or Firm—Mario A. Monaco; Harry E. Westlake, Jr.

[57] ABSTRACT

Invention relates to improved processes for preparing 5-fluoro-2-methyl-1-(p-methylsulfinylbenzylidene)-indenyl-3-acetic acid, to intermediates thereof, and to the preparation of said intermediates.

7 Claims, No Drawings

PROCESS OF PREPARING 5-FLUORO-2-METHYL-1-(PARAMETHYLSUL-FINYLBENZYLIDENE)-INDENYL-3-ACETIC ACID

BACKGROUND OF THE INVENTION 5-fluoro-2-methyl-1-(p-methylsulfinylbenzylidene)-idenyl-3-acetic acid is a known compound having anti-inflammatory activity described in U.S. Pat. No. 3,654,349. Previously, this compound has been prepared by condensing an appropriately substituted benzaldehyde with an acetic acid ester in a Claisen reaction or with an alpha-halogenated propionic acid ester in a Reformatsky reaction. The resulting unsaturated ester was reduced and hydrolyzed to give a beta-aryl propionic acid which is subsequently ring closed to form the indanone. The aliphatic side chain was then introduced by a Reformatsky or Wittig reaction and the 1-substituent was introduced into the resultant indenyl acetic acid or ester by reacting said acetic acid derivative with an aromatic aldehyde or ketone of the desired structural formula and dehydrating to form the desired indenyl acetic acid.

It is an object of this invention to provide new processes of preparing 5-fluoro-2-methyl-1-(p-methylsulfinylbenzylidene)-indenyl-3-acetic acid from starting materials with the acetic acid side chain already incorporated.

SUMMARY OF THE INVENTION

This invention relates to novel processes for preparing 5-fluoro-2-methyl-1-(para-methylsulfinylbenzylidene)-indenyl-3-acetic acid, its derivatives and to intermediates thereof.

One aspect of the invention is the preparation of 5-fluoro-2methyl-1-(para-methylsulfinylbenzylidene)-indenyl-3-acetic acid from 5-fluoro-2-methyl-indanol-3-acetic acid. The indanol-3-acetic acid is dehydrated to the corresponding indene-3-acetic acid; and the indene-3-acetic acid is condensed with para-methylthiobenzaldehyde followed by oxidation of the thio group or alternatively with para-methylsulfinylbenzaldehyde to produce 5-fluoro-2-methyl-1-(para-methylsulfinyl-benzylidene)-indenyl-3-acetic acid.

Another aspect of the invention is the preparation of 5-fluoro-2-methyl-1-(para-methylsulfinylbenzylidene)-indenyl-3-acetic acid from 5-fluoro-2-methyl-indanone-3-acetic acid. The indanone-3-acetic acid is reduced to the corresponding 5-fluoro-2-methyl-indanol-3acetic acid. The indanol-3-acetic acid is treated as above to produce the final product.

Another aspect of the invention is the preparation of 5-fluoro-2-methyl-1-(para-methylsulfinylbenzylidene)-indenyl-3-acetic acid from 4-(para-fluorobenzoyl)-3-pentenoic acid. The 4-(para-fluorobenzoyl)-3-pentenoic acid is cyclized under Friedel-Crafts conditions to form 5-fluoro-2-methyl-indanone-3-acetic acid; the indanone-3-acetic acid is treated as above to produce the final product.

Another aspect of the invention is the preparation of 5-fluoro-2-methyl-1-(para-methylsulfinylbenzylidene)-indenyl-3-acetic acid from gamma-(para-fluorobenzoyl)-gamma-valerolactone. The gamma-(para-fluorobenzoyl)-gamma-valerolactone is cyclized to form 5-fluoro-2-methyl-indanone-3-acetic acid; the indanone-3-acetic acid is treated as above to produce 5-fluoro-2-methyl-1-(para-methylsulfinylbenzylidene)-indenyl-3-acetic acid.

Another aspect of the invention is the process of preparing 5-fluoro-2-methyl-1-(para-methylsulfinylbenzylidene)-indenyl-3-acetic acid from gamma-carboxy-gamma-valerolactone, gamma-carboxy-gamma-valerolactone anhydride or gamma-carbonyl halide-gamma-valerolactone. The valerolactone is used to acylate fluorobenzene to form gamma-(para-fluorobenzoyl)-gamma-valerolactone. The gamma-(para-fluorobenzoyl)-gamma-valerolactone is treated as above to produce the final product.

Another aspect of the invention is the process of preparing 5-fluoro-2-methyl-1-(para-methylsulfinyl-benylidene)-indenyl-3-acetic acid from gamma-methylglutaconic anhydride. The gamma-methylglutaconic anhydride is used to acylate fluorobenzene to form 4-(para-fluorobenzoyl)-3-pentenoic acid. The pentenoic acid is treated as above to produce the final product.

Another aspect of the invention is the process of preparing 5-fluoro-2-methyl-1-(para-methylsulfinylbenzylidene)-indenyl-3-acetic acid from angelica lactone. Carbon monoxide reacts with angelica lactone to form a valerolactone which

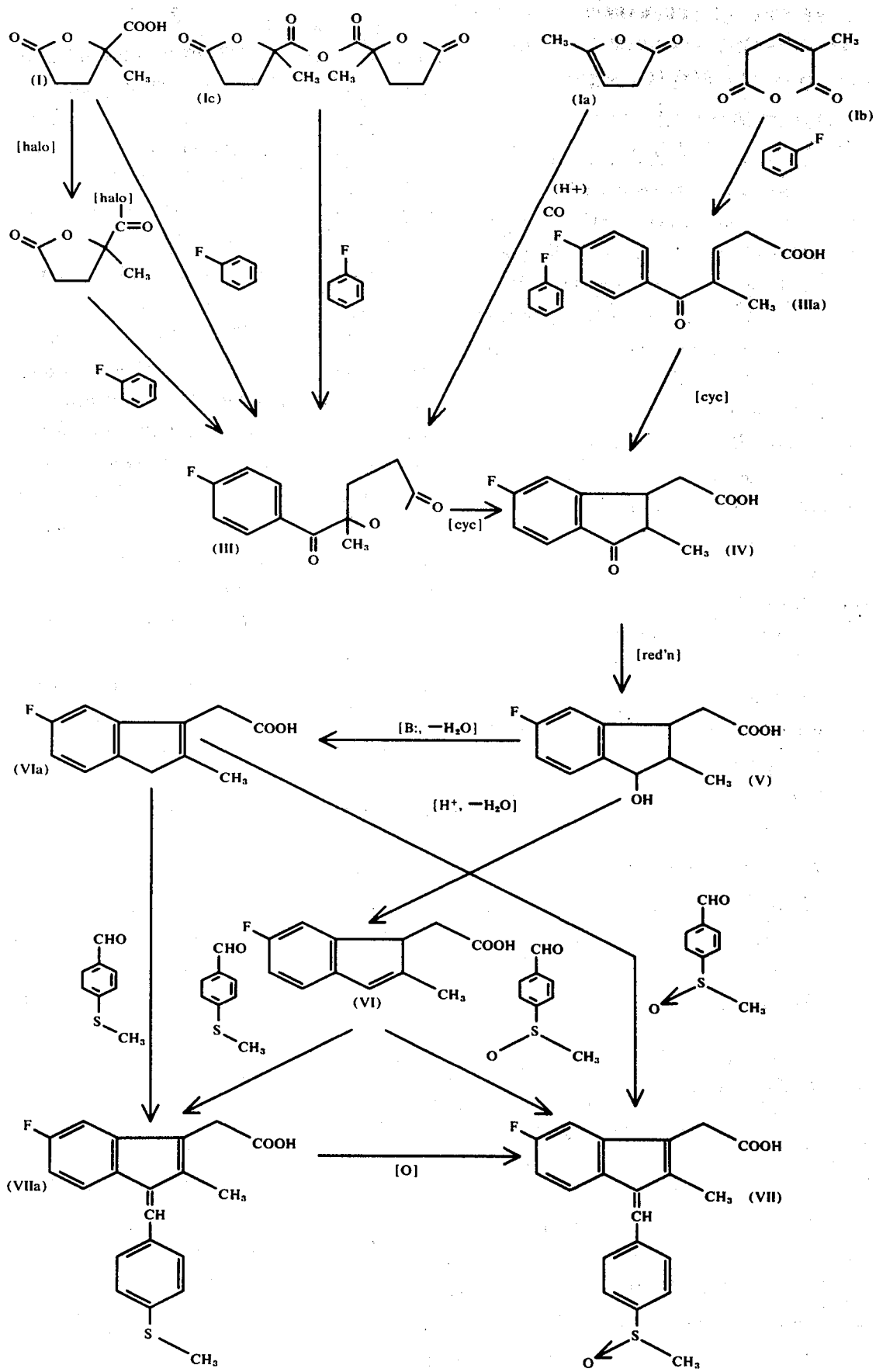

is used to acylate fluorobenzene to form gamma-(para-fluorobenzoyl)-gamma-valerolactone. The gamma-(para-fluorobenzoyl)-gamma-valerolactone is treated as above to produce the final product.

Another aspect of the invention is the novel intermediate compounds produced during the novel synthetic process for preparing 5-fluoro-2-methyl-1-(para-methylsulfinylbenzylidene)-indenyl-3-acetic acid. The novel intermediate compounds are: gamma-carbonyl halide-gamma-valerolactone, gamma-(para-fluorobenzoyl)-gamma-valerolactone, 4-(para-fluorobenzoyl)-3-pentenoic acid; 5-fluoro-2-methyl-indanol-3-acetic acid; and 5;-fluoro-2-methyl-ind-1-ene-3-acetic acid.

DETAILS OF THE INVENTION

In accordance with this invention it has been found that the subject compound may be readily prepared by converting gamma-carboxy-gamma-valerolactone (I) a known compound disclosed by Adams and Hauserman, *Journal of the American Chemical Society*, 74, 649 [1952] to the corresponding gamma-carbonyl halide-gamma-valerolactone (II), a novel compound, by halogenation. The acid halide is then used to acylate fluorobenzene using a Lewis Acid catalyst to produce the gamma-(para-fluorobenzoyl)-gamma-valerolactone (III), a novel compound, which in turn is cyclized to form 5-fluoro-2-methyl-indanone-3-acetic acid (IV). The 5-fluoro-2-methyl-indanone-3-acetic acid (IV) is reduced by either catalytic or chemical methods to produce the corresponding alcohol, 5fluoro-2methyl-indanol-3-acetic acid (V), a novel compound, which is dehydrated via acid catalysis to produce 5-fluoro-2-methyl-ind-1-ene-3acetic acid (VI), or via base catalysis to produce 5-fluoro-2-methyl-ind-2-ene-3-acetic acid (VIa). The indene-3-acetic acid (VI) or (VIa) is condensed with paramethylthiobenzaldehyde followed by oxidation or with para-methylsulfinylbenzaldehyde, followed by acidification to form cis-5-fluoro-2-methyl-1-(para-methylsulfinylbenzylidene)-idenyl3-acetic acid (VII). The para-methylsulfinylbenzaldehyde may be prepared by oxidizing para-methylthiobenzaldehyde with a suitable oxidizing agent, such as hydrogen peroxide.

The gamma-carboxy-gamma-valerolactone (I) is converted to the corresponding gamma-carbonyl halide-gamma-valerolactone (II) by reaction with a halogenating agent such as phosphorous trihalide, phosphorus pentahalide, carbonyl halide or thionyl halide. The reaction takes place over a temperature range of from about 0° to to the boiling point of the system, preferably from about 40° to 75° C. The preferred halogenating agents are thionyl chloride and carbonyl chloride (phosgene). The reaction may be carried out neat, in an inert solvent or mixtures thereof. Non-aqueous solvents are preferred since the halogenating reagent may be chemically changed by water necessitating increased amounts of reagent. Suitable solvents include hydrocarbons, polyhalogenated hydrocarbons, nitrated hydrocarbons, dialkyl amides and mixtures thereof. Preferred solvents include nitrobenzene, orthodichlorobenzene, chloroform, methylene dichloride, carbon tetrachloride, hexane and dimethylformamide (DMF). When DMF is used as a solvent, the active halogenating agent is the reaction product of DMF and the halogenating agent (listed above) also known as the Vilsmeier reagent. The Vilsmeier reagent is the preferred halogenating agent and is formed in situ when at least a catalytic amount of DMF is present. The reaction is preferably carried out neat in the presence of a catalytic amount of DMF. Although all the acid halides may be produced, the preferred halides are chloride and bromide. The concentration of the halogenating reagent is not critical. From 1.0 to 10.0 moles of halogenating agent are used per mole of gamma-carboxy-gamma-valerolactone, perferably 1.0 to 3.0 moles. The rate of the reaction is dependent upon the temperature at which it is carried out. The reaction time is not critical and generally the reaction is run until it is substantially complete. Pressure is not critical to this reaction and generally the reaction is carried out in an open system at atmospheric pressure. The acid halide product of the reaction may be isolated from the reaction mixture using conventional techniques, preferably by distillation.

The Friedel-Crafts acylation of fluorobenzene with the gamma-carbonyl halide-gamma-valerolactone (II) may be carried out with an excess of fluorobenzene, with an inert solvent such as carbon disulfide, polyhalogenated hydrocarbon, hydrocarbon or nitrohydrocarbon or mixtures thereof. Non-aqueous solvents are preferred since the catalyst may be chemically changed by water necessitating increased amounts of catalyst. Preferred solvents include dichloroethane, chloroform, methylene dichloride, orthodichlorobenzene, nitrobenzene, carbon disulfide and hexane. The reaction takes place over a temperature of from about 0° to the boiling point of the system, preferably between 5° and 25° C. The rate of the reaction is dependent upon the temperature at which is carried out. Reaction time is not critical and generally the reaction is run until it is substantially complete. The acylation is catalyzed by Lewis Acids such as gallium trihalides, aluminum trihalides, antimony trihalides, titanium tetrahalides, boron trihalides and iron trihalides. The catalyst concentration is from about 0.001 moles to 10.0 moles per mole of valerolactone, preferably from 0.01 to 3.0 moles. Preferred catalysts include aluminum trichloride and aluminum tribromide. The fluorobenzene is normally the reactant present in an excess amount. The excess fluorobenzene, which also acts as a solvent, favors the desired product. The acid halide is normally added to the mixture of fluorobenzene and catalyst, although the catalyst may be added to the mixture of the acid halide and fluorobenzene or the fluorobenzene may be added to the catalyst and the acid halide. More than one equivalent of catalyst to acid halide is required for the reaction to take place with 2.0 equivalents being the amount theoretically required for the reaction. Preferably, from about 2 to 3 equivalents of aluminum trihalide are used and particularly about 2.2 to 2.5 equivalents. Pressure is not critical to the reaction. Generally, the reaction would be carried out under atmospheric pressure in an open system. The product of the Friedel-Crafts acylation is gamma-(para-fluorobenzoyl)-gamma-valerolactone (III).

Although the acid chloride (II), is generally used to acylate the fluorobenzene, it is possible to use the acid (I) or the acid anhydride (Ic) in like manner. when a Lewis Acid catalyst is used with the acid (I) or the anhydride (Ic) an additional amount of catalyst should be used as a greater proportion of the catalyst is tied up in complexes with the starting material. The amount of the Lewis acid catalyst should be increased by 50% when the acid (I) is employed as the starting material, and by 100% when the anhydride (Ic) is employed as the starting material. When using gamma-carboxygamma-valerolactone (I) the following may optionally be used as catalysts in addition to those listed above: hydrogen fluoride, sulfuric acid and polyphosphoric acid.

Gamma-(para-fluorobenzoyl)-gamma-valerolactone (II) may be prepared from angelica lactone (Ia). The angelica lactone (Ia) is reacted with carbon monoxide under a pressure of from about 5 to 200 atmospheres of carbon monoxide in the presence of at least a catalytic amount of a protonic acid or one of the Lewis Acids listed above, such as sulfuric acid to produce an activated species of gamma-carboxy-gamma-valerolactone (I*) which may react with an acid present (HX) to produce a valerolactone. For example, when HX is water (HOH) gamma-carboxy-gamma-valerolactone (I) is produced, and when HX is a halo acid, gamma-carbonyl halide-gamma-valerolactone (II) is produced.

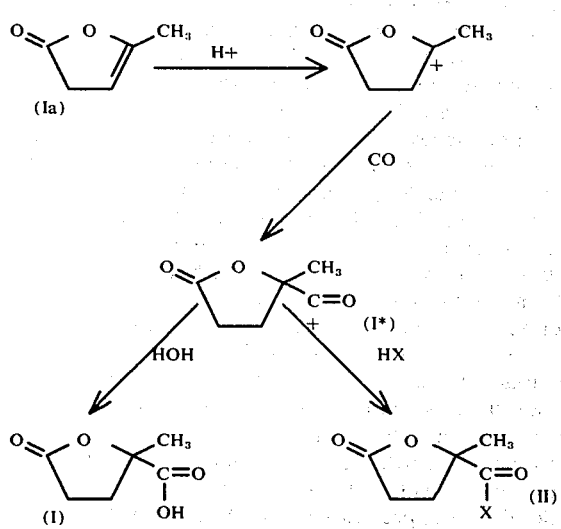

The acid catalyst concentration is from about 0.001 moles to 10.0 moles per mole of angelica lactone (I), and preferably 0.01 mole to 3.0 mole. The reaction takes place over a temperature range of from about 0° to 200° C, preferably 10° to 35° C. The reaction mixture is stirred from about 2 to 20 minutes and fluorobenzene is introduced. The reaction may use an excess of fluorobenzene as the solvent, or an inert non-aqueous organic solvent may be employed, such as a hydorcarbon, polyhalogenated hydrocarbon, or carbon disulfide or mixtures thereof. Preferred solvents include hexane, methylene dichloride and carbon disulfide. The rate of reaction is dependent upon the temperature at which it is carried out. Reaction time is not critical and generally the reaction is run until it is substantially complete. The product of the reaction is gamma-(para-fluorobenzoyl)-gamma-valerolactone (III) which may be used to produce the 5-fluoro-2-methyl-1-(para-methylsulfinylbenzylidene)-indenyl-3-acetic acid (VII) in the manner described above.

The gamma-(para-fluorobenzoyl)-gamma-valerolactone (III) is cyclized by heating with a Lewis Acid catalyst to a temperature of from about 80° to 200° C, preferably 105°–180° C. The rate of reaction is dependent upon the temperature at which it is carried out. Reaction time is not critical and generally the reaction is run until it is substantially completed. The Lewis Acids used as catalysts are those some acids which are used in the Friedel-Crafts acylation above, preferably, aluminum trihalides and especially aluminum trichloride. The catalyst is present in a concentration of 0.001 to 10.0 moles per mole of valerolactone (III) preferredly in the range of 0.01 to 3.0 moles.

The cyclization may be carried out in a solvent such as a halogenated hydrocarbon, nitrated hydrocarbon or a molten salt. Preferred solvents include ortho-dichlorobenzene, nitrobenzene and nitromethane or a molten mixture of sodium chloride-aluminum chloride, particularly ortho-dichlorobenzene. The pressure is not critical to this reaction. Generally, the reaction is carried out under atmospheric pressure in an open system. The reaction produces a mixture of 5-fluoro-2-methyl-indanone-3-acetic acid and 5-fluoro-indanone-2-propionic acid, with the indanone-3-acetic predominating when the reaction is carried out at the higher temperature.

The cyclization may be carried out in the same reaction vessel as the acylation by adding additional catalyst, if necessary, to replace that amount destroyed and heating the reaction mixture to cyclize the valerolactone (III). When combining the two steps it is preferable to use a high boiling solvent which may be heated to the higher temperatures required for cyclization, such as ortho-dichlorobenzene.

An alternate starting material for the preparation of 5-fluoro-2-methyl-indanone-3-acetic acid (IV) is 4-(para-fluorobenzoyl)-3-pentenoic acid (IIIa), a novel compound. The 4-(para-fluorobenzoyl)-3-pentenoic acid (IIIa) is prepared by acylating fluorobenzene with gamma-methylglutaconic anhydride, a known compound, under Friedel-Crafts conditions. The acylation may be carried out neat, in an inert non-aqueous solvent or mixtures thereof. Examples of the types of solvents used are excess fluorobenzene, polyhalogenated hydrocarbons, hydrocarbons and carbon disulfide. Preferred solvents include ortho-dichlorobenzene, methylene dichloride, carbon disulfide and hexane. The acylation may be carried out from about 0° and 85° C, preferably between 70° to 85° C. The rate of reaction is dependent upon the temperature at which it is carried out. Reaction time is not critical and generally the reaction is run until it is substantially complete. Pressure is not critical to the reaction. Generally the reaction is carried out under atmospheric pressure in and open system. Lewis Acid catalyst such as are listed above are employed, preferably the aluminum halides. The catalyst concentration is from about 0.001 moles to about 10.0 moles per mole of glutaconic anhydride, preferably 0.01 to 3.0 moles. The 4-(para-fluorobenzoyl)-3-pentenoic acid (IIIa) is cyclized to form 5-fluoro-2-methyl-indanone-3-acetic acid (IV) in the same manner as the gamma-(para-fluorobenzoyl)-gamma-valerolactone (III), described above.

The 5-fluoro-2-methyl-indanone-3-acetic acid (IV) may be reduced by either chemical or catalytic means to 5-fluoro-2-methyl-indanol-3-acetic acid (V). Suitable reagents include alkali metal borohydrides, aluminum isopropoxide and hydrogen using a suitable hydrogenation catalyst, such as finely divided nickel, platinum or palladium. The chemical reaction is carried out in a suitable inert solvent such as water, alcohol, or mixtures thereof depending on the nature of the reducing agent. The preferred reducing agent is sodium borohydride in water which has been made alkaline. The reducing agent is present in a concentration of from 0.25 to 3 moles per mole of indanone (IV), preferably from 1.2-2.0 moles. Examples of suitable solvents are alkaline water, methanol, ethanol and particularly isopropanol. The reaction may be carried out at a temperature from about 0° to 85° C, preferably between 40° C and 82° C. The rate of reaction is dependent upon the temperature at which it is carried out. Reaction time is not critical and generally the reaction is run until it is substantially complete. The pressure is not critical to the chemical reduction. Generally, the reaction would be carried out under atmospheric pressure in an open system.

The reduction of 5-fluoro-2-methyl-indanone-3-acetic acid (IV) may also be carried out by catalytic hydrogenation. The reaction is carried out using a suitable hydrogenation catalyst such as finely divided nickel, iridium, rhenium, ruthenium, rhodium, platinum or palladium or a reduced metal oxide thereof and hydrogen under a pressure of from atmospheric to 200 atmospheres, preferably atmospheric to 10 atmospheres in a closed system. The catalyst concentration is from 0.1 to 10 percent by weight of the indanone (II), preferably from 1 to 5%. The reaction may be carried out with a solvent. Suitable solvents include saturated hydrocarbons, alcohols, esters, and alkaline water and mixtures thereof, such as hexane, methanol, ethanol, ethyl acetate and alkaline water. The catalyst may be either supported on a carrier such as charcoal or the finely divided metal powder or reduced metal oxide thereof. The rate of reaction is dependent upon the temperature at which it is carried out. Reaction time is not critical and generally the reaction is run until it is substantially complete. The alcohol (V) is not normally isolated from the solvent mixture but is reacted as is in the next step of the reaction. 5-fluoro-2-methyl-indanol-3-acetic acid (V) may be dehydrated under acid or base conditions, preferably acidic conditions by heating to form 5-fluoro-2-methyl-ind-1-ene3-acetic acid (VI) a novel compound. Both organic and inorganic acids may be used, preferably mineral acids, alkyl sulfonic acids and aryl sulfonic acids such as para-tolenesulfonic acid, hydrochloric acid, sulfuric acid and methanesulfonic acid. The acid concentration is from 0.001 mole to 10 moles per mole of indanol (V) preferably 0.01 to 0.2 moles.

The acidic dehydration may be carried out in an inert organic solvent such as hydrocarbons or halogenated hydrocarbons, or mixtures thereof. Preferred solvents include ethylbenzene, toluene and xylene and particularly benzene.

Alternatively, the dehydration may be done under basic conditions to produce the ind-2-ene. Suitable bases include sodium alkoxides, sodamide, potassium alkoxides, alkali metal hydroxides, and alkaline earth hydroxides, such as sodium methoxide, sodium ethoxide, potassium hydroxide, sodium hydroxide, potassium methoxide, and potassium ethoxide. The base concentration is from 0.1 mole to 100 moles per mole of indanol (V) preferably 3.0 to 10 moles. The basic dehydration may be carried out in an inert organic solvent such as alcohols, ethers and mixtures thereof. Suitable solvents include glyme, diglyme, triglyme, methanol, ethanol, isopropanol and tert-butanol, with the preferred solvents ethanol and isopropanol.

The dehydration may be carried out between 20° and 150° C, preferably between 60° and 100° C. The rate of reaction is dependent upon the temperature at which it is carried out. Reaction time is not critical and generally the reaction is run until it is substantially complete.

The pressure is not critical to this reaction, although atmospheric pressure or less is preferred since a molecule of water is eliminated. Generally, the reaction is carried out at atmospheric pressure in an open system. The dehydration under acid conditions produces the ind-1-ene (VI) a novel compound, while dehydration under basic conditions produces the ind-2-ene (VIa) a known compound.

The introduction of the benzylidene substituent on the indene acetic acid compound (VI or VIa) is conveniently carried out by reaction with para-methylsulfinyl (or para-methylthio)benzaldehyde in the presence of a strong base at a temperature of from 0° to 100° C and preferably from 20° to 80° C in the presence of a solvent. The ratio of aldehyde to indene is suitably about 1 to 2:1, but preferably about 1.5:1 and the ratio of base to indene may vary from a catalytic amount to equimolar or more. Strong bases such as alkali and alkaline earth hydroxides or $C_{1-5}$ alkoxides such as NaOH, $KOCH_3$, KOtBu, tetra $C_{1-6}$ alkyl ammonium hydroxides or benzyl tri $C_{1-5}$-alkyl ammonium hydroxides, such as benzyltrimethylammonium hydroxide, and alkali metal hydrides may be suitably used. Suitable solvents are polar solvents such as dimethoxyethane, methanol, pyridine, dimethylformamide and the like and non-polar solvents such as benzene, toluene, xylene and the like.

The thus prepared benzylidene indene acetic acid salt is converted to the free acid during work-up. The conversion may be carried out under generally known acid conditions such as in the presence of strong organic acids (para-toluenesulfonic acid, trifluoroacetic acid) or mineral acids (hydrochloric, sulfuric) especially hydrochloric acid.

Where the para-methylthiobenzaldehyde is used in the condensation, the oxidation of the methylthio group to the desired methylsulfinyl group may be carried out by any number of standard techniques, such as oxidation with $H_2O_2$, basic periodates and hypohalites (preferably the alkaline or alkaline earth periodates and hypohalites) or organic peracids, such as peracetic acid and monoperphthalic acid, but especially with $H_2O_2$. The reaction is preferably carried out in the presence of a solvent. For such purposes, $C_{1-5}$ alkanoic acids (acetic acid), halogenated hydrocarbons (chloroform, 1,2-dichloroethane), ethers (dioxane), $C_{1-5}$ alkanols (isopropanol) or mixtures thereof may be used. The mole ratio of oxidizing agent to indene acetic acid compound may be from 0.5 to 10 but preferably from 0.8 to 1.5. The reaction time and temperature are not critical, the reaction being carried out until the reaction is substantially completed. The pressure is not critical to this reaction. Generally, the reaction would be carried out under atmospheric pressure in an open system.

The last three steps, namely the reduction of the indanone, the dehydration of the indanol, and the condensation of the indene may be carried out without isolating the products in the same reaction vessel. The three steps may all be carried out under basic conditions or it is possible to acidify the reaction for the dehydration step only.

The following examples are given by way of illustration.

EXAMPLE 1

Gamma-carbonyl chloride-gamma-valerolactone (II)

A partial solution of 12.0 g (0.832 moles of gamma-carboxy-gamma-valerolactone (I) and 12.0 g (1.01 mole) of distilled thionyl chloride is treated with 5 drops of DMF (dimethylformamide) and then heated at 50° C until no more gas is evolved (about 6 hours). Vacuum is applied to the system to remove unreacted thionyl chloride and then the product is distilled to give gamma-carbonyl chloride-gamma-valerolactone, (II) boiling point 85–6° C/ 0.9 mm Hg, as a colorless liquid.

Similarly, when an equivalent amount of phosphorous trichloride, phosphorous pentachloride, or carbonyl chloride is used in place of the thionyl chloride in the above example, similar results are obtained.

Similarly, when an equivalent amount of phosphorous tribromide, phosphorous pentabromide, carbonyl bromide or thionyl bromide is used in place of thionyl chloride in the above example, the gamma-carbonyl bromide-gamma-valerolactone is obtained.

EXAMPLE 2

Gamma-(para-fluorobenzoyl)-gamma-valerolactone (III)

77.8 g (0.478 moles) of gamma-carbonyl chloride-gamma-valerolactone (II) is added dropwise to a suspension of 147 g (1.10 moles) of aluminum chloride and 138 g (1.43 moles) of fluorobenzene which is maintained at a temperature of 12°–15° C. The suspension is stirred for an additional hour at 12°–15° C after the addition is completed and for an additional 15 hours at ambient temperature. The slushy mixture is cooled to 10° C and 100 ml of diethyl ether is added (heat kick) to give a solution. The solution is poured into a mixture of ice and hydrochloric acid, more diethyl ether is added, and the layers are separated. The aqueous layer is back extracted with diethyl ether. The ether extracts are combined and washed with hydrochloric acid (2M), $H_2O$, sat'd. aqueous $NaHCO_3$ (2 times), $H_2O$, dried and concentrated to give a wet, yellow solid.

The solid is dissolved in 100 ml isopropanol at 45° C, cooled, seeded and allowed to stand at 5° C for 2 hours. 100 ml of hexane is added. The solution is aged for 1 hour at 5° C, filtered, washed with 60 ml 1/1 isopropanol/hexane, 60 ml hexane and dried in vacuo to give a white solid, melting point 48.5°–50° C.

The mother liquor from above is dissolved in 75 ml of isopropanol and cooled in the refrigerator to given a 2-phase solution (i.e. product oiled out). The 2-phase mixture is seeded, allowed to stand for 3 days, filtered, washed three times with 50/50 isopropanol/ hexane, then twice with hexane and dried to give a white solid.

Similarly, when an equivalent amount of aluminum bromide is used in place of aluminum chloride in the above example, similar results are obtained.

EXAMPLE 3

Gamma-(para-fluorobenzoyl)-gamma-valerolactone (III)

To 0.5 moles of fluorobenzene and 0.2 moles of sulfuric acid at 80° C is added portionwise 0.2 , moles of gamma-carboxy-gamma-valerolactone (I). The mixture is kept at 80° C for an additional hour. The mixture is cooled to 10° C and 100 ml of ether is added. The mixture is poured onto ice and 100 ml of ether is added. The layers are separated and the aqueous layer is back extracted with ether and the ether extracts are combined. The combined ether extracts are washed with water, saturated sodium bicarbonate (twice), water, dried and concentrated to give the crude product (III).

Similarly, when an equivalent amount of hydrofluoric acid, polyphosphoric acid or one of the Lewis Acids listed above, such as aluminum chloride or aluminum bromide is used in place of the sulfuric acid, similar results are obtained. When either aluminum chloride or aluminum bromide are used, the reaction product is poured into a mixture of ice and hydrochloric acid. When the Lewis Acids are used as catalyst 0.64 moles of catalysts are required.

EXAMPLE 4

Gamma-(para-fluorobenzoyl)-gamma-valerolactone (III)

To a stirred solution of 0.5 moles of fluorobenzene and 0.2 moles of gamma-carboxy-gamma-valerolactone anhydride (Ic) is added 0.9 moles of anhydrous aluminum chloride powder portionwise to maintain a moderate reflux rate. After the addition is complete the reaction mixture is heated at reflux for an additional hour. The mixture is cooled to 10° C and 100 ml of ether is added. The mixture is poured into a mixture of ice and hydrochloric acid and 100 ml of ether is added. The layers are separated and the aqueous layer is back extracted with ether and the ether extracts are combined. The combined ether extracts are washed with hydrochloric acid (2M), water, saturated sodium bicarbonate (twice), water, dried and concentrated to give the crude product (III).

Similarly, when an equivalent amount of aluminum bromide is used in place of the aluminum chloride, similar results are obtained.

EXAMPLE 5

4-(para-fluorobenzoyl)-3-pentenoic acid (IIIa)

To a stirred solution of 126 g (1.0 moles) of gamma-methylglutaconic anhydride (Ib) and 192.2 g (2.0 mole) of fluorobenzene is added 306.6 g (2.3 mole) of anhydrous aluminum chloride powder poritonwise to maintain a moderate reflux rate. After the addition is complete the mixture is heated on a steam bath for 5 minutes. The mixture is cooled and then 400 ml of water is added slowly followed by 100 ml of concentrated of HCl. 200 ml of ether is added and the organic layer is separated and washed with two 400ml portions of water. The organic layer is dried and concentrated in vacuo to yield the crude product. Chromatography on alumina affords the pure 4-(para-fluorobenzoyl)-3-pentenoic acid (IIIa).

Similarly, when an equivalent amount of aluminum bromide is used in place of aluminum chloride in the above example, similar results are obtained.

Similarly, when a catalytically effective amount of polyphosphoric acid, hydrogen fluoride, sulfuric acid, fluoroboric acid, boron trifluoride, boron trichloride, or boron tribromide is used in place of the aluminum chloride in the above example, similar results are obtained.

EXAMPLE 6

5-fluoro-2-methyl-indanone-3-acetic acid (IV)

A solution of 111.1 g (0.50 moles) of 4-(para-fluorobenzoyl)-3-pentenoic acid in 150 ml of orthodichlorobenzene is added dropwise to a mixture of 153.2 g (1.15 moles) of aluminum chloride and 200 ml of ortho dichlrorobenzene. The resulting mixture is heated at 100° C. for 1 hour. The reaction mixture is cooled and poured into ice and 2M hydrochloric acid. The organic layer is separated and washed successively with water (twice) and saturated sodium bicarbonate (twice). The combined bicarbonate extracts containing the product are carefully acidified with hydrochloric acid. Diethyl ether is added and the organic layer is separated and washed with water, dried and concentrated in vacuo to give the crude product, which may be recrystallized from an etherhexane mixture to give the pure indanone.

Similarly, when an equivalent amount of aluminum bromide is used in place of the aluminum chloride in the above examples, similar results are obtained.

Similarly, when a catalytic amount of hydrogen fluoride, polyphosphoric acid, or sulfuric acid is used in place of the aluminum chloride in the above example, similar results are obtained.

EXAMPLE 7

5-fluoro-2-methyl-indanone-3-acetic acid (IV)

A solution of 2.096 g (9.4 mmoles) of gamma-(para-fluorobenzoyl)-gamma-valerolactone (III), 2.760 g (20.7 mmoles, 2.2 equivalents) of anhydrous aluminum chloride and 8.0 ml of distilled ortho-dichlorobenzene is heated to reflux for 10 minutes (gas is till evolved but at a much slower rate than at the beginning). The solution is cooled to room temperature and poured into ice and 2M hydrochloric acid. The aqueous solution is extracted with ether. The ether extract is washed with 2M hydrochloric acid, water and saturated sodium bicarbonate. The basic aqueous extracts contain the acid product. The basic aqueous solution is washed with ether, neutralized with hydrochloric acid, extracted with methylene dichloride, dried and concentrated to give 5-fluoro-2-methyl-indanone-3-acetic acid (IV).

Similarly, when a equivalent amount of aluminum bromide is used in place of aluminum chloride, similar results are obtained.

Similarly, when a catalytically effective amount of hydrogen fluoride, polyphosphoric acid or sulfuric acid is used in place of aluminum chloride in the above example, similar results are obtained.

EXAMPLE 8

5-fluoro-2-methyl-indanol-3-acetic acid (V)

A solution of 390 mg (1.8 mmoles) of 5-fluoro-2-methyl-indanone-3-acetic acid (IV) in 6 ml of isopropanol is made basic by the addition of 2.5 M sodium hydroxide (to about pH 9 to 10). To this solution is added 100 mg of sodium borohydride (2.6 mmoles). The solution is stirred at ambient temperature for 80 minutes and at 60° C for 45 minutes. The solution is poured into 2M hydrochloric acid and extracted with methylene dichloride. The organic layer is dried and concentrated to give 5-fluoro-2-methyl-indanol-3-acetic acid (V).

Similarly, when an equivalent amount of lithium borohydride or potassium borohydride is used in place of sodium borohydride in the above examples, similar results are obtained.

EXAMPLE 9

5-fluoro-2-methyl-indanol-3-acetic acid (V)

To a solution of 390 mg (1.8 mmoles) of 5-fluoro-2-methyl-indanone-3-acetic acid (V) in 6 ml of isopropanol is added 250 mg of platinum oxide. The hydrogenation is run on a Paar apparatus at ambient temperature at 40 psig, until the reaction is completed (30 minutes). The solution is filtered, dried and concentrated to give 5-fluoro-2-methyl-indanol-3-acetic acid (VI).

Similarly, when an equivalent amount of nickel or palladium is used in place of platinum oxide in the above examples, similar results are obtained.

EXAMPLE 10

5-fluoro-2-methyl-ind-1-ene-3-acetic acid (VI)

A solution of 387 mg of 5-fluoro-2-methyl-indanol-3-acetic acid (V) in 10 ml of benzene, to which 50 mg of para-toluenesulfonic acid (p-TsOH·$H_2O$) is added is heated to reflux for 85 minutes during which time 3 ml of solvent is allowed to distill. The solution is allowed to cool, diluted with methylene dichloride, and washed with water. The organic solution is dried and concentrated to give 5-fluoro-2-methyl-ind-1ene-3-acetic acid (VI).

Similarly, when an equivalent amount of hydrochloric, sulfuric or methanesulfonic acid is used in place of para-toluenesulfonic acid in the above example, similar results are obtained.

EXAMPLE II

5-fluoro-2-methyl-ind-2-ene-3-acetic acid (VIa)

A solution of 390 mg of 5-fluoro-2-methyl-indanol-3-acetic acid (V) in 10 ml of water, to which 400 mg of potassium hydroxide has been added, is heated to reflux for 5 hours. The solution is allowed to cool acidified with 2N hydrochloric acid, and extracted with methylene dichloride. The organic solution is dried and concentrated to give 5-fluoro-2-methyl-ind-2-ene-3-acetic acid (VIa).

Similarly when an equivalent amount of sodium hydroxide or sodium ethoxide is used in place of potassium hydroxide in the above example, similar results are obtained.

EXAMPLE 12

5-fluoro-2-methyl-1-(para-methylthiobenzylidene)-indenyl-3-acetic acid (VIIa)

To 0.01 moles of 5-fluoro-2-methyl-ind-1-ene-3-acetic acid (VI) and 0.01 moles of para-methylthiobenzaldehyde is added 2.0 equivalents of 25% methanolic sodium methoxide. The mixture is refluxed for 2 hours, cooled, neutralized with acetic acid and diluted with water. The reaction mixture is extracted into ethyl acetate which is washed with water and concentrated to yield the crude product (VIIa).

Similarly, when an equivalent amount of sodium hydroxide, potassium hydroxide, sodium hydride, potassium hydride, sodium ethoxide or benzyltrimethylammonium hydroxide is used in place of sodium methoxide in the above example, similar results are obtained.

EXAMPLE 13

5-fluoro-2-methyl-1-(para-methylsulfinylbenzylidene)-indenyl-3-acetic acid (VII)

Sodium metaperiodate trihydrate (0.0422 moles) in water (8.5ml) is added to 5-fluoro-2-methyl-1-(para-methylthiobenzylidene)-indenyl-3-acetic acid (VIIa) (0.01 moles) in 240 ml of methanol and 10 ml of acetone at room temperature. The mixture is stirred overnight and then concentrated to a small volume, diluted with water and filtered. The precipitate is washed with water and dried in air.

Similarly, when an equivalent amount of hydrogen peroxide, a hypohalite or an organic peracid such as peracetic acid or monoperphtahlic acid is used in place of sodium metaperiodate in the above reaction, similar results are obtained.

EXAMPLE 14

5-fluoro-2-methyl-1-(para-methylsulfinylbenzylidene)-indenyl-3-acetic acid (VII)

To 0.01 moles of 5-fluoro-2-methyl-ind-1-ene-3-acetic acid (VI) and 0.01 moles of para-methylsulfinylbenzaldehyde is added 2.0 equivalents of 25% methanolic sodium methoxide. The mixture is refluxed for 2 hours cooled and neutralized with acetic acid and diluted with water. The reaction mixture is extracted into ethyl acetate which is washed with water and concentrated to yield the crude product (VII).

Similarly, when an equivalent amount of sodium hydroxide, potassium hydroxide, sodium hydride, potassium hydride, sodium ethoxide or benzyltrimethylammonium hydroxide is used in place of sodium methoxide in the above example, similar results are obtained.

EXAMPLE 15

Gamma-(para-fluorobenzyl)-gamma-valerolacton (III)

A mixture of 50 g (0.51 moles) of angelica lactone (Ia) and 1 ml of concentrated sulfuric acid in an autoclave is pressurized to 150 atmospheres with carbon monoxide. The mixture is stirred for 10 minutes and 49.0 g (0.51 moles) of fluorobenzene introduced dropwise over a period of 1 hour. The autoclave is vented, and the contents are partitioned between diethyl ether and water. The organic (ether layer) is washed with water, saturated sodium bicarbonate, water, dried and concentrated to give gamma-(para-fluorobenzoyl)-gamma-valerolactone (III).

Similarly, when an equivalent amount of hydrobromic acid, hydrochloric acid, hydrofluoric acid, phosphoric acid, trifluoroacetic acid or trichloroacetic acid is used in place of the sulfuric acid, similar results are obtained.

Similarly, when a catalytically effective amount of aluminum chloride or aluminum bromide is used in place of sulfuric acid, similar results are obtained.

EXAMPLE 16

5-fluoro-2-methyl-indanone-3-acetic acid (IV)

To a stirred solution of 138 g (1.43 moles, 3 equivalents) of fluorobenzene and 68 g (0.47 moles) of gamma-carboxy-gamma-valerolactone is added 206 g (1.55 moles, 3.3 equivalents) of aluminum chloride portionwise. The resulting mixture is heated to reflux for 5 hours. 150 ml of ortho-dichlorobenzene is added to the reaction mixture and the mixture is heated to distill off the excess fluorobenzene. The reaction is heated to reflux for 10 minutes. The reaction mixture is cooled to room temperature and poured into a mixture of ice and 2N hydrochloric acid, water and saturated sodium bicarbonate. The basic aqueous extract containing the acid product is washed with ether, neutralized with 2N hydrochloric acid, dried and concentrated to give 5-fluoro-2-methyl-indanone-3-acetic acid (IV).

Similarly, when an equivalent amount of aluminum bromide, is used in place of aluminum chloride, similar results are obtained.

Similarly, when a catalytically effective amount of anhydrous hydrofluoric acid, polyphosphoric acid or sulfuric acid is used in place of aluminum chloride, similar results are obtained.

Similarly, when an equivalent amount of nitrobenzene is used in place of ortho-dichlorobenzene, similar results are obtained.

EXAMPLE 17

5-fluoro-2-methyl-indanone-3-acetic acid (IV)

A mixture of 147 g (1.10 moles, 2.3 equiv.) of aluminum chloride and 138 g (1.43 moles, 3 equiv.) of fluorobenzene is cooled to 15° C. 68.8 g (0.478 mole) of gamma-carbonyl chloride-gamma-valerolactone (II) is added dropwise to the vigorously stirred suspension while keeping the temperature at 10° to 15° C. After the addition is complete, the reaction is allowed to warm to ambient temperature and is stirred overnight. 150 ml of orthodichlorobenzene is added to the reaction mixture and the mixture is heated to distill off the excess fluorobenzene. The reaction is heated to reflux for 10 minutes. The reaction mixture is cooled to room temperature and poured into a mixture of ice and 2N hydrochloric acid. The reaction mixture is extracted with diethyl ether. The ether extract is washed with 2N hydrochloric acid, water and saturated sodium bicarbonate. The basic aqueous extract containing the acid product is washed with ether, neutralized with 2N hydrochloric acid, dried and concentrated to give 5-fluoro-2-methyl-indanone-3-acetic acid (IV).

Similarly, when an equivalent amount of aluminum bromide is used in place of aluminum chloride, similar results are obtained.

Similarly, when an equivalent amount of nitrobenzene is used in place of ortho-dichlorobenzene, similar results are obtained.

EXAMPLE 18 5-fluoro-2-methyl-indanone-3-acetic acid (IV)

A mixture of 147 g (1.10 moles, 2.3 equiv) of aluminum chloride and 138 g (1.43 moles, 3 equiv) of fluorobenzene is cooled to 15° C. 72.9 g (0.27 moles) of gamma-carboxy-gamma-valerolactone anhydride (Ic) is added dropwise to the vigorously stirred suspension while keeping the temperature at 10° to 15° C. After the addition is complete, the reaction is allowed to warm to ambient temperature and is stirred overnight. 150 ml of orthodichlorobenzene is added to the reaction mixture and the mixture is heated to distill off the excess fluorobenzene. The reaction is heated to reflux for 10 minutes. The reaction mixture is cooled to room temperature and poured into a mixture of ice and 2N hydrochloric acid. The reaction mixture is extracted with diethyl ether. The ether extract is washed with 2N hydrochloric acid, water and saturated sodium bicarbonate. The basic aqueous extract containing the acid product is washed with ether, neutralized with 2N hydrochloric acid, dried and concentrated to give crude 5-fluoro2methyl-indanone-3-acetic acid (IV).

Similarly, when an equivalent amount of aluminum bromide is used in place of aluminum chloride, similar results are obtained.

Similarly, when an equivalent amount of nitrobenzene is used in place of ortho-dichlorobenzene, similar results are obtained.

EXAMPLE 19

5-fluoro-2-methyl-1-(para-methylsulfinylbenzylidene)-indenyl-3-acetic acid (VII)

A solution of 0.01 mole of 5-fluoro-2-methyl-indanone-3-acetic acid (IV) in 6 ml of isopropanol is made basic by the addition of 2.5M sodium hydroxide (to about pH 9 to 10). To this solution is added 0.015 moles of sodium borohydride. The solution is stirred at ambient temperature for 80 minutes and at 60° C for 45 minutes. The solution is made acidic by the addition of 6M hydrochloric acid (to about pH 1 to 2), and heated to reflux for 30 minutes. The solution is allowed to cool and basified with sodium hydroxide to a pH of about 13.0. To the solution is added 0.01 mole of paramethylsulfinylbenzaldehyde and 2.0 equivalents of sodium hydroxide. The mixture is refluxed for 2 hours, cooled, neutralized with acetic acid and diluted with water. The reaction mixture is extracted into ethyl acetate which is washed with water and concentrated to yield the crude product (VII).

Similarly when an equivalent amount of potassium borohydride or lithium borohydride is used in place of sodijm borohydride or sulfuric acid, para-toluenesulfonic acid or methanesulfonic acid is used in place of hydrochloric acid or potassium hydroxide, is used in place of sodium hydroxide in the above example, similar results are obtained.

What is claimed is:
1. A process of preparing 5-fluoro-2-methyl-1para-methylsulfinylbenzylidene)-indenyl-3-acetic acid which comprises the steps of:
    a. acylating fluorobenzene with gamma-carbonylhalide-gamma-valerolactone, gamma-carboxy-gamma-valerolactone or gamma-carboxy-gamma-valerolactone anhydride in the presence of gallium trihalide, aluminum trihalide, antimony trihalide, titanium tetrahalide, boron trihalide or iron trihalide to form gamma-(para-fluorobenzoyl)-gamma-valerolactone; or acylating fluorobenzene with gamma-methyl-glutaconic anhydride in the presence of aluminum chloride, polyphosphoric acid, hydrogen fluoride, sulfuric acid, fluoroboric acid, boron trifluoride, boron trichloride or boron tribromide at a temperature of from 0°–85° C to form 4-(para-fluorobenzoyl)-3-pentenoic acid;
    b. cyclizing said gamma-(para-fluorobenzoyl)-gamma-valerolactone or said4-(para-fluorobenzoyl)-3-pentenoic acid at a temperature of from 80°–200° C in an inert solvent in the presence of gallium trihalide, aluminum trihalide, antimony trihalide, titanium tetrahalide, boron trihalide or iron trihalide to form 5-fluoro-2-methyl-indanone-3-acetic acid;
    c. reducing said 5-fluoro-2-methyl-indanone-3-acetic acid in the presence of alkali metal borohydride, aluminum isopropoxide or in the presence of nickel, iridium, rhenium, ruthenium, rhodium, platinum or palladium or a reduced metal oxide thereof and hydrogen under a pressure of from atmospheric to 200 atmospheres in the presence of an inert solvent to form 5-fluoro-2-methyl-indanol-3-acetic acid;
    d. dehydrating said 5-fluoro-2-methyl-indanol-3-acetic acid at a temperature of from 20°–150° C in the presence of an inert solven under acid conditions to form 5-fluoro-2-methyl-ind-1-ene-3-acetic acid or under basic conditions to form 5-fluoro-2-methyl-ind-2-ene-3-acetic acid;
    e. condensing said 5-fluoro-2-methyl-indene acetic acid in the presence of a strong base in an inert solvent with para-methylthiobenzaldehyde followed by oxidation or with para-methyl-sulfinylbenzaldehyde, followed by acidification to produce the desired product.

2. The process of claim 1 wherein the fluorobenzene is acylated with gamma-carboxy-gamma-valerolactone.

3. The process of claim 1 wherein the fluorobenzene is acylated with gamma-carboxy-gamma-valerolactone anhydride.

4. The process of claim 1 wherein the fluorobenzene is acylated with gamma-carbonyl halide-gamma-valerolactone.

5. A process of preparing 5-fluoro-2-methyl-1-(para-methyl-sulfinylbenzylidene)-indenyl-3-acetic acid which comprises the steps of:
    a. acylating fluorobenzene with gamma-carbonylhalide-gamma-valerolactone, gamma-carboxy-gamma-valerolactone or gamma-carboxy-gamma-valerolactone anhydride in the presence of gallium trihalide, aluminum trihalide, antimony trihalide, titanium tetrahalide, boron trihalide or iron trihalide to form gamma-(para-fluorobenzoyl)-gamma-valerolactone;
    b. cyclizing said gamma-(para-fluorobenzoyl)-gamma-valerolactone at a temperature of from 80°–200° C in an inert solvent in the presence of gallium trihalide, aluminum trihalide, antimony trihalide, titanium tetrahalide, boron trihalide or iron trihalide to form 5-fluoro-2-methyl-indanone-3-acetic acid;
    c. reducing said 5-fluoro-2-methyl-indanone-3-acetic acid in the presence of alkali metal borohydride, aluminum isopropoxide or in the presence of nickel, iridium, rhenium, ruthenium, rhodium, platinum or palladium or a reduced metal oxide thereof and hydrogen under a pressure of from atmospheric to 200 atmospheres in the presence of an inert solvent to form 5-fluoro-2-methyl-indanol-3-acetic acid;
    d. dehydrating said 5-fluoro-2-methyl-indanol-3-acetic acid at a temperature of from 20°–150° C in the presence of an inert solvent under acid conditions to form 5-fluoro-2-methyl-ind-1-ene-3-acetic acid or under basic conditions to form 5-fluoro-2-methyl-ind-2-ene-3-acetic acid;
    e. condensing said 5-fluoro-2-methyl-indene-3-acetic acid in the presence of a strong base in an inert solvent with para-methylthiobenzaldehyde followed by oxidation or with para-methyl-sulfinylbenzaldehyde, followed by acidification to produce the desired product.

6. The process of claim 5 wherein the 5-fluoro-2-methyl-indene-3-acetic acid is condensed with para-methylthiobenzaldehyde.

7. The process of claim 5 wherein the 5-fluoro-2-methyl-indene-3-acetic acid is condensed with para-methylsulfinylbenzaldehyde.

* * * * *

UNITED STATES PATENT AND TRADEMARK OFFICE
CERTIFICATE OF CORRECTION

PATENT NO. : 3,998,875
DATED : December 21, 1976
INVENTOR(S) : Roger J. Tull and David G. Melillo It is certified that error appears in the above-identified patent and that said Letters Patent are hereby corrected as shown below:

Under "INVENTORS" the last name of the second inventor should be "MELILLO".

Column 18, line 11, "5-fluoro-2-methyl-indene acetic" should read "5-fluoro-2-methyl-indene-3-acetic".

Signed and Sealed this

Twenty-ninth Day of March 1977

[SEAL]

Attest:

RUTH C. MASON
*Attesting Officer*

C. MARSHALL DANN
*Commissioner of Patents and Trademarks*